United States Patent [19]

Kocal

[11] Patent Number: 5,334,793
[45] Date of Patent: * Aug. 2, 1994

[54] INCREASING CATALYST LIFE AND IMPROVING PRODUCT LINEARITY IN THE ALKYLATION OF AROMATICS WITH LINEAR OLEFINS

[75] Inventor: Joseph A. Kocal, Gurnee, Ill.

[73] Assignee: UOP, Des Plaines, Ill.

[ * ] Notice: The portion of the term of this patent subsequent to Sep. 14, 2010 has been disclaimed.

[21] Appl. No.: 67,900

[22] Filed: May 27, 1993

Related U.S. Application Data

[63] Continuation-in-part of Ser. No. 919,329, Jul. 27, 1992, Pat. No. 5,245,094.

[51] Int. Cl.$^5$ .............................................. C07C 2/66
[52] U.S. Cl. ................... 585/323; 585/464; 585/467; 585/800; 585/805
[58] Field of Search ............... 585/323, 324, 464, 467, 585/804, 800, 805

[56] References Cited

U.S. PATENT DOCUMENTS

| | | | |
|---|---|---|---|
| 5,185,486 | 2/1993 | Collin et al. | 585/323 |
| 5,210,348 | 5/1993 | Hsieh et al. | 585/446 |
| 5,245,094 | 9/1993 | Kocal | 585/804 |

OTHER PUBLICATIONS

R. A. Meyers, "Handbook of Petroleum Refining Processes", McGraw-Hill Book Company (1986), 4–36 to 4–38 and 1–39 to 1–41.

Ullman's Encyclopedia of Industrial Chemistry, 5th Ed., V.A. 13, Verlagsgesellschaft mbH (1989) pp. 234, 242–243 and pp. 259–260.

Kirk-Othmer Encyclopedia of Chemical Technology, 3rd Ed., V. 16, J. Wiley & Sons, (1981) p. 492.

"Encyclopedia of Chemical Processing and Design", J. J. McKetta, Editor, V. 14 M. Dekker, Inc. (1982), pp. 276–289.

*Primary Examiner*—Anthony McFarlane
*Attorney, Agent, or Firm*—Thomas K. McBride; Eugene I. Snyder

[57] ABSTRACT

It has been found that the aromatic byproducts normally formed in the dehydrogenation of normal paraffins to linear monoolefins are detrimental in the usual processes of aromatic alkylation using the dehydrogenation product mixture as an alkylation feedstock. In particular, when solids are used as the alkylation catalysts with recycle of the unreacted feedstock to the dehydrogenation reactor the aromatic byproducts increase to a level where they exert a significant decrease in the stability of the alkylation catalyst. When the aromatic byproducts are removed in whole or in part alkylation may be performed at a substantially lower temperature, which affords alkylated aromatics whose alkyl portion has greater linearity than that observed at a higher alkylation temperature.

18 Claims, 1 Drawing Sheet

INCREASING CATALYST LIFE AND IMPROVING PRODUCT LINEARITY IN THE ALKYLATION OF AROMATICS WITH LINEAR OLEFINS

CROSS REFERENCE TO RELATED APPLICATION

This application is a continuation-in-part of my co-pending application, U.S. Ser. No. 07/919,329, filed Jul. 27, 1992, now U.S. Pat. No. 5,245,094, all of which is hereby incorporated by reference

BACKGROUND OF THE INVENTION

Over fifty years ago it was recognized that alkylbenzene sulfonates (ABS) were quite effective detergents superior to natural soaps in many respects. Because of their lower price, their price stability, and their effectiveness in a wide range of detergent formulations, ABS rapidly displaced soaps in household laundry and dishwashing applications and became the standard surfactants for the detergent industry.

The alkylbenzene sulfonates had substantial branching in the alkyl chain until the early 1960's when it became apparent that these detergents were contributing to the pollution of lakes and streams and forming relatively stable foams. Examination of the problem showed that alkyl chains with a branched structure were not susceptible to rapid biodegradation and the surfactant properties of the detergent thus persisted for long periods of time. This was contrary to the earlier situation when natural soaps were used because the linear alkyl chains in natural soaps underwent rapid biodegradation.

After recognizing the biodegradability of ABS based on alkylation by linear olefins, industry turned its attention to the production of these unbranched olefins and their subsequent use in the production of linear alkylbenzenes. Processes were developed for efficient alkylation of benzene by available feedstocks containing linear olefins, and the production of linear alkylbenzenes (LABs) became another reliable process broadly available to the petroleum and petrochemical industry. It gradually evolved that HF-catalyzed alkylation was particularly effective in LAB production, and an HF-based alkylation process became the industry standard.

At this point the definition of several terms are necessary to adequately understand and appreciate what follows. Alkylation typically is performed using an excess of benzene relative to olefins. The ideal process would afford 100% conversion of olefins using an equimolar proportion of benzene and olefins, but since this is not attained one strives for maximum olefin conversion using a benzene to olefin molar ratio up to about 30. The better the process, the lower will be the benzene:olefin ratio at a high conversion of, say, 98%. The degree of conversion at a constant value of benzene-olefin ratio is a measure of catalytic activity (subject to the caveat that the ratio must not be so high that the degree of conversion is invariant to small changes in this ratio). The degree of conversion may be expressed by the formula, $$V = C/T \times 100,$$

where V equals percent conversion, C equals moles of olefin consumed, and T equals moles olefin initially present.

However active the catalyst may be, a process based on the catalyst also must be selective. Selectivity is defined as the percentage of total olefin consumed under reaction conditions which appears as monoalkylbenzene and can be expressed by the equation, $$S = M/C \times 100,$$

where S equals selectivity, M equals moles of monoalkylbenzenes produced, and C equals moles olefin consumed. The better the selectivity, the more desirable the process. An approximate measure of selectivity is given by the equation, $$S = \frac{\text{weight monoalkylbenzene}}{\text{weight total products}} \times 100$$

where "total products" includes monoalkylbenzenes, polyalkylbenzenes, and olefin oligomers. At high selectivity (S>85%) the results calculated from the two equations are nearly identical. The latter of the foregoing two equations is routinely used in commercial practice because of the analytical difficulty in distinguishing between oligomers and polyalkylbenzenes.

Finally, the reaction of linear olefins with benzene in principal proceeds according to the equation, $$C_6H_6 + R_1CH=CHR_2 \rightarrow C_6H_5CH(R_1)CH_2R_2 + C_6H_5CH(R_2)CH_2R_1.$$

Note that the side chain is branched solely at the benzylic carbon and contains only one branch in the chain. Although strictly speaking this is not a linear alkylbenzene, nonetheless the terminology which has arisen for the process and product in fact includes as linear alkylbenzenes those materials whose alkyl group chemically arises directly from linear olefins and therefore includes alpha-branched olefins. Because alkylation catalysts also may induce the rearrangement of olefins to ultimately give products which are not readily biodegradable (vide supra), for example, $\alpha,\alpha$-disubstituted olefins which subsequently react with benzene to afford an alkylbenzene with branching at other than the benzylic carbon,

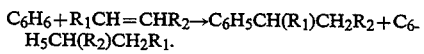

 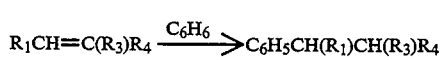

the degree to which the catalyst effects formation of linear alkylbenzenes is another important catalyst parameter. The degree of linearity can be expressed by the equation, $$D = L/M \times 100,$$

where D equals degree of linearity, L equals moles of linear monoalkylbenzene produced, and M equals moles of total monoalkylbenzene produced.

Consequently, the ideal process is one where V equals 100, S equals 100, and D equals 100. The linearity requirement is assuming added importance and significance in view of the expectation in some areas of minimum standards for linearity in detergents of 92–95% near-term, increasing to 95–98% by about the year 2000. Since the olefinic feedstock used for alkylation generally contains a small percentage of non-linear olefins—a non-liner olefin content of about 2% is common to many processes—the requisite linearity in the detergent alkylate places even more stringent requirements on catalytic performance; the inherent linearity of the alkylation process must increase by the amount of non-linear olefins present in the feedstock. For example, with a feedstock containing 2% non-linear olefins the catalyst must effect alkylation with 92% linearity in order to afford a product with 90% linearity, and with a feedstock containing 4% non-linear olefins the catalyst must effect alkylation with 94% linearity to achieve the same result.

The invention described and claimed within leads, inter alia, to increased linearity of alkylbenzene sulfonates. Although the result of increased linearity is simple, clear, and incontrovertible, its origin is at first blush obscure and mysterious, and we need to take a brief sojourn into the origin of the linear olefins used as the feedstock for LAB processes so that we may see in bold relief the problem which we faced and appreciate how its solution, which is our invention, leads to a substantial improvement in LAB processes.

The linear olefins used to react with benzene in a LAB process generally arise from the dehydrogenation of linear paraffins, or normal paraffins. Generally the dehydrogenation reaction is not run to completion in order to minimize cracking, isomerization, and other byproducts, and the entire dehydrogenation product mixture is used as the feedstock to an alkylation zone. The polyolefins formed during dehydrogenation are minimized when the dehydrogenation product mixture is used as the alkylation feedstock for LAB production, often by a separate selective hydrogenation process. Consequently the alkylation feedstock is a mixture largely of unreacted paraffins, small amounts (approximately 2% or less) of branched olefins, unbranched and linear monoolefins of the same carbon number (typically C6–C20 range) as the normal paraffins which are dehydrogenated, and small amounts of aromatic byproducts which have the same carbon number as the paraffins which are dehydrogenated, that is, C6–C20 aromatics. Although it has been known for some time that these aromatic byproducts are formed in the catalytic dehydrogenation of paraffins (e.g., see the article starting at page 86 of the Jan. 26, 1970 issue of "Chemical Engineering"), we have only recently observed that they have a significant deleterious effect on a LAB process. Therein hangs our tale, and we now turn our attention to these previously recognized but unappreciated aromatic byproducts of normal paraffin dehydrogenation.

Although our invention is generally applicable to alkylation using linear olefins in the C6–C20 range, for LAB production alkylation feedstocks containing C8–C16 olefins, and especially C10–C14 olefins, are most preferred, and for simplicity of presentation and clarity of exposition we shall focus on the C10–C14 materials with the proviso that our description is applicable, with only minor modifications if any, to the broader range of materials of C6–C20. The aromatic byproducts in question include alkylated benzenes, polyalkylbenzenes, naphthalenes, other polynuclear aromatic hydrocarbons, alkylated polynuclear hydrocarbons in the C10–C14 range, indanes, and tetralins, that is, they are aromatics of the same carbon number as the paraffin being dehydrogenated and may be viewed as aromatized normal paraffins. In the general case the aromatic byproducts contain from 6 up to about 20 carbon atoms, but because the C6 member is benzene, which is the aromatic most often being alkylated, it is only the aromatic byproducts of 7 through about 20 carbon atoms which concern us here. Typically these aromatic byproducts are formed to the extent of perhaps 0.2–0.7% in a dehydrogenation unit. However, as the flow scheme typical for LAB processes of FIG. 1 shows, at least a portion of the unreacted alkylation feedstock is recycled to the dehydrogenation unit, leading to the accumulation of the aromatic byproducts so that at steady state conditions they are present in the alkylation feedstock at concentrations typically on the order of 3–6 weight percent where HF is the alkylation catalyst and 4–10 percent where a solid alkylation catalyst is used.

We have observed that the aromatic byproducts, especially at their steady state concentration, in the alkylation feedstock substantially reduce the activity of an alkylation catalyst, thereby substantially reducing the useful lifetime (stability) of an alkylation catalyst. A common measure of catalyst stability in detergent alkylation is the number of hours the catalyst will afford 100% (i.e., 99+%) conversion of the olefins in the alkylation feedstock at an otherwise unvarying set of reaction conditions (benzene to olefin ratio, temperature, space velocity, etc.). With increasing concentration of aromatic byproducts in the alkylation feedstock the number of hours a catalyst effects 100% conversion decreases. Conversely, reducing the concentration of the aromatic byproducts in the alkylation feedstock increases catalyst stability, i.e., the number of hours a catalyst effects 100% conversion increases.

The number of hours a particular catalyst will continue to effect 100% conversion increases with temperature, Therefore, the customary solution to a decrease in catalyst stability is to increase operating temperature. The corollary of this is that if an increase in catalyst stability can be effected by an independent means then the operating temperature may be decreased. Therefore, a consequence of the resulting increased catalyst stability arising from a reduced concentration of aromatic byproducts in the alkylation feedstock is that one can decrease alkylation temperature without any adverse effects. Recently we have observed that the degree of linearity in linear alkylbenzenes is more highly dependent on the alkylation temperature than on, for example, the nature of the alkylation catalyst. Therefore, any process change which permits a lower alkylation temperature leads to an increase in linearity of LABs. It follows that a consequence of reducing the concentration of aromatic byproducts in the alkylation feedstock is to afford LABs with a higher linearity because of a reduction in alkylation temperature made possible by the increase in catalyst stability attending the reduced aromatic byproduct concentration.

Thus our invention is simple; reduce the concentration of aromatic byproducts present in alkylation feedstocks used for LAB production. The result of our invention is simply and significantly an increased linearity of LABs. These favorable results arrive in a highly circuitous fashion which the foregoing explanation hopefully makes clear and unmistakable.

As important as is the increased linearity afforded by our invention it is not the sole benefit conferred, for another outcome of reducing aromatic byproducts is an increased selectivity of alkylation. Since the olefins in the alkylation feedstock constitute a high value item the increased selectivity translates directly to an economic benefit. As will also become apparent from the following description there are still other benefits ancillary to our invention which makes its practice highly advantageous.

SUMMARY OF THE INVENTION

The purpose of our invention is principally to increase the linearity of alkyl aromatics formed in the continuous alkylation of aromatics with linear monoolefins present in an alkylation feedstock arising from the dehydrogenation of normal paraffins and which also contains unreacted normal paraffins and aromatic byproducts of dehydrogenation. An ancillary purpose is to increase the selectivity of monoalkylaromatic formation. An embodiment comprises using as the alkylation feedstock a mixture which contains less than 2 weight percent aromatic byproducts. In a more specific embodiment the concentration of aromatic byproducts is less than about 1 weight percent. In a more specific embodiment the steady state concentration of aromatic byproducts in the alkylation feedstock is less than about 1 weight percent and the alkylation temperature is decreased at least 5° C. Other purposes and embodiments will become apparent from our ensuing description.

DESCRIPTION OF THE INVENTION

Figure 1:
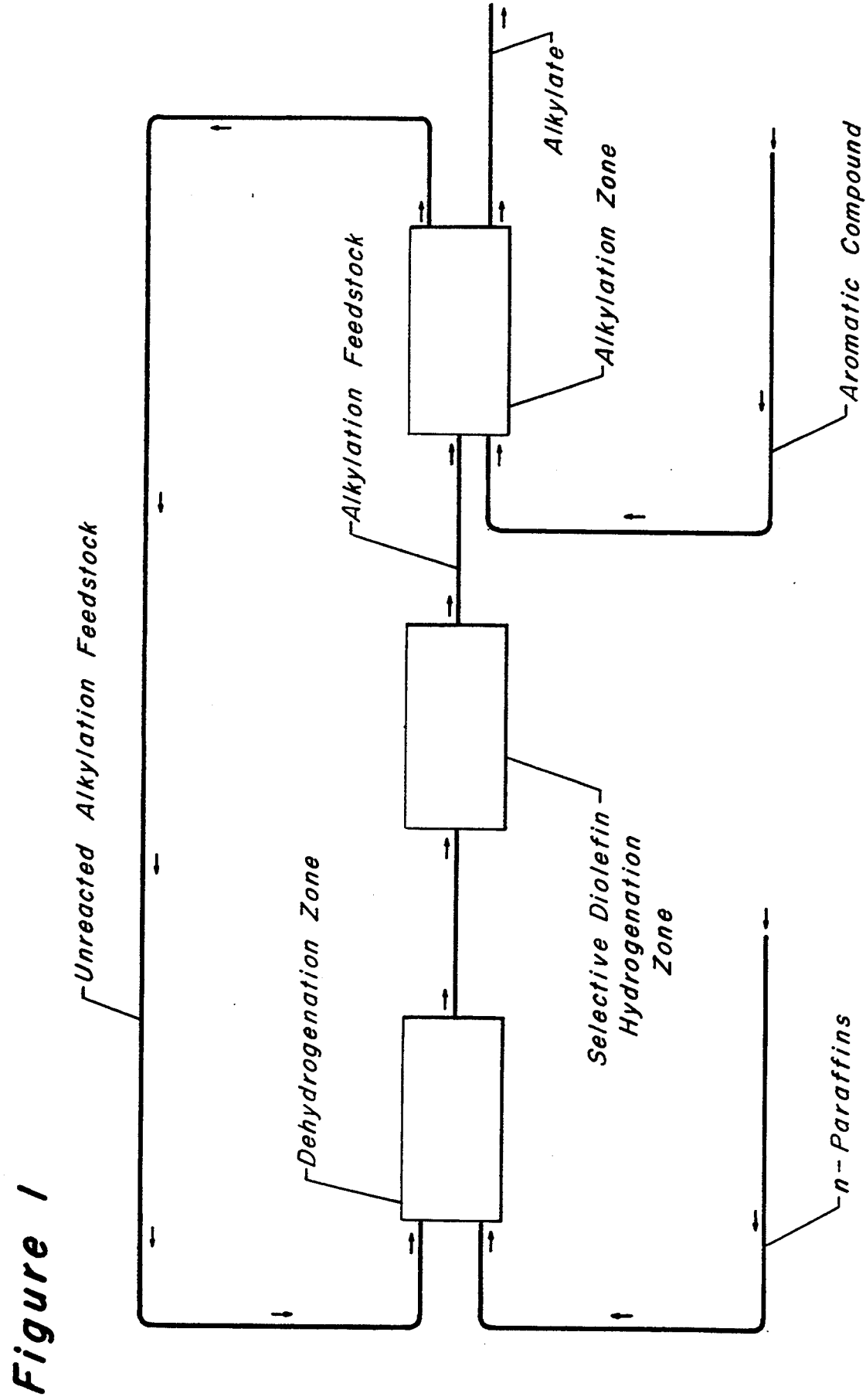
FIG. 1 is a typical flow scheme for linear alkylbenzene production by alkylation of benzene using linear monoolefins.

A common feedstock used for the alkylation of an aromatic substrate, especially for the alkylation of benzene, and particularly for the alkylation of benzene to linear alkylbenzenes, is one arising from the dehydrogenation of normal paraffins and which usually contains linear olefins as the major alkylating species, substantial and usually major amounts of unreacted paraffins, and minor amounts of branched olefins, possibly diolefins, and aromatic byproducts of the same carbon number as the paraffin being dehydrogenated. Since only part of the alkylation feedstock contains components which react with the aromatic substrate, the remainder of the alkylation feedstock is generally recycled to the dehydrogenation zone and in the course of this process the aromatic byproducts build to a steady state concentration in the alkylation feedstock up to perhaps 10 weight percent. We have now found that the aromatic byproducts decrease the stability of alkylation catalysts, and substantial process benefits are derived from removing them in whole or in part.

Although the reason for the observed phenomenon has not been proven, our working hypothesis is that alkylation catalysts have strong acid sites which are particularly active in effecting alkylation, and which are blocked by the aromatic byproduct. Consequently, as the concentration of alkylated byproducts present in the alkylation feedstock increases the activity of the alkylation catalyst is gradually and continually decreased through blockage of the active sites. The higher the alkylation temperature, the less effective are the aromatic byproducts in blocking strongly acidic sites; thus, higher operating temperatures are required to prevent or mitigate catalyst deactivation. But the higher alkylation operating temperatures unavoidably and inevitably lead to a lower linearity in the formed monoalkylated aromatics. Conversely, if the aromatic byproducts are removed active site blockage occurs to a lesser extent, lower alkylation operating temperatures can be used since catalyst deactivation and instability are no longer a problem, and at the lower alkylation operating temperatures the resulting product has a higher degree of linearity, which is a desirable and much sought-after result. Hence our invention.

The alkylation feedstocks of interest in this application contain at least one linear olefin and arise from the dehydrogenation of at least one normal (i.e., linear) paraffin. Since dehydrogenation is a well known process, both from a technical and commercial aspect, it is unnecessary to give a lengthy description here. General references thereto may be found in R. A. Meyers, "Handbook of Petroleum Refining Processes", McGraw-Hill Book Company (1986), 4-36 to 4-38; Ullman's Encyclopedia of Industrial Chemistry, 5th Ed., V. A. 13, Verlagsgesellschaft mbH (1989) pp. 234, 242-243; Kirk-Othmer Encyclopedia of Chemical Technology, 3rd Ed., V, 16, J. Wiley & Sons (1981) p. 492; "Encyclopedia of Chemical Processing and Design", J. J. McKetta, Editor, V. 14, M. Dekker, Inc., (1982) pp. 276-289. For our purposes it is important to note that dehydrogenation of normal paraffins generally is carried out to conversions of under about 30% in order to minimize formation of products other than linear olefins. Consequently, the dehydrogenation product stream generally contains large amounts of unreacted normal paraffins and smaller amounts of linear olefins of the same carbon number as the normal paraffins. The linear olefins and the paraffins normally are in the 6-20 carbon range, although the C8-C16, and especially the C10-C14, range olefins are of primary interest in the production of LABs. In addition to the linear olefins the stream also may contain smaller amounts of branched olefins, resulting from the isomerization of either the normal paraffins or the linear olefins, diolefins, and aromatic byproducts which result from aromatization of the paraffins and have the same carbon number as the normal paraffins in the feedstock charged to the dehydrogenation unit. The dehydrogenation product mixture may be used directly as the alkylation feedstock or, what is perhaps more common, the diolefins in the dehydrogenation product mixture may be selectively hydrogenated to monoolefins with the resulting selective hydrogenation product mixture used as the alkylation feedstock.

Many dehydrogenation catalysts are known in the art as exemplified by those cited or described in U.S. Pat. No. 3,274,287, 3,315,007, 3,315,008, 3,745,112, and 4,430,517, as well as references cited therein. However, it is important to note that whatever dehydrogenation catalyst is used there are formed aromatic byproducts generally to the extent of no more than 1%, and usually in the range of 0.2-0.7 weight percent of the dehydrogenation product mixture. As previously mentioned, these aromatic byproducts include alkylbenzenes, polynuclear hydrocarbons, and alkylated polynuclear hydrocarbons having the same carbon number as the components in the normal paraffin feedstock. Of particular importance in the preparation of LABs are aromatic byproducts having from 8 through 16 carbon atoms, especially those with 10 through 14 carbon atoms. Even though these materials are formed to the extent of less than 1% in the dehydrogenation process, because at least part of the unreacted portion of the alkylation feedstock is recycled to the dehydrogenation unit (vide infra) the aromatic byproducts accumulate in the alkylation feedstock and eventually reach a steady state concentration generally not less than about 2 weight percent and as high as about 10 weight percent. The steady state concentration of the aromatic byproducts will depend largely on the particular catalyst used in the alkylation zone as well as the extent of recycle from the alkylation zone to the dehydrogenation zone.

A common variant in LAB processes is to selectively hydrogenate the diolefins that are normally present in the dehydrogenated product stream prior to using the stream as an alkylation feedstock. Selective diolefin hydrogenation converts the diolefins to monoclefins, which are the desired product of the dehydrogenation section, and produces a product stream containing only monoclefins which is subsequently used as the alkylation feedstock. Selective hydrogenation methods and catalysts in the context of this discussion also are well known in the art as exemplified by U.S. Pat. No. 4,523,048 and references cited therein.

It needs to be repeated that the alkylation feedstock contains not only the components formed in a single pass through a dehydrogenation zone and, where used, a selective diolefin hydrogenation zone, but also contains components which accumulate because of recycle of at least part of the product stream from the alkylation of the aromatic, most usually to the dehydrogenation zone. In particular, the recycle stream contains aromatic byproducts which are formed in the dehydrogenation zone, are passed through the alkylation zone unchanged, and are recycled with the remainder of the unreacted alkylation feedstock stream to the front end or dehydrogenation zone of a typical continuous LAB process scheme. Consequently, the alkylation feedstocks of interest in this invention are those containing more than 2 weight percent of aromatic byproducts.

The mixture from the dehydrogenation zone of normal paraffins and linear olefins containing small amounts of branched olefins, possibly diolefins, and aromatic byproducts is used as the alkylation feedstock for the alkylation of an aromatic compound in an alkylation zone. Of particular interest is the alkylation of benzene, especially using an alkylation feedstock containing linear olefins in the C8–C16 range, and especially those in the C10–C14 range, for the resulting monoalkylbenzenes are used as the precursors for alkylbenzene sulfonates. Of special importance are the linear alkylbenzenes because of the biodegradability of the linear alkylbenzene sulfonates which are used as detergents. The alkylation of aromatics, especially LAB production, also is a well known process that need not be described in great detail here. See R. A. Meyers, op. cit., 1–39 to 1–41; Ullman's Encyclopedia of Industrial Chemistry, op cit., V. A13, pp. 259–260. Although liquid HF long has been the catalyst of choice, solid alkylation catalysts have been known for some time and are gaining favor as the environmental concerns regarding HF become more important. Many solid materials having activity as alkylation catalysts are well known to those practicing the alkylation art and it is unnecessary to describe these materials here in any great detail. Examples of such solid alkylation catalysts, which are illustrative rather than exhaustive, include materials such as silica-aluminas, crystalline aluminosilicates such as zeolites and molecular sieves, naturally occurring and synthetic clays, including pillared clays, sulfated oxides such as sulfated zirconia, traditional Friedel-Crafts catalysts, such as aluminum chloride and zinc chloride, and solid Lewis acids generally.

Whatever the catalyst used, alkylation generally is performed at a temperature, $T_1$, affording at least 98% conversion of olefin, and generally over about 99%, at a molar ratio of aromatic substrate to olefin generally between about 5 and about 30. Alkylation temperature will, of course, depend on the catalyst used but will be in the range of 10°–150° C. Since alkylation is performed with a liquid feedstock, the minimum reaction pressure will depend upon alkylation temperature as well as the nature of the feedstock. In any event, this is readily determined by the skilled worker. Any pressure above this minimum will suffice, i.e., the reaction pressure is a non-critical variable which has no significant effect on alkylation so long as alkylation is conducted in the liquid phase. Space velocities usually are in the range of 0.5–50 $hr^{-1}$. Restricting our attention for the moment to solid alkylation catalysts, the aromatic byproducts in the alkylation feedstock generally deactivate such catalysts steadily, presumably by blocking their strong acid sites. Whatever the mechanism, it is found that the alkylation temperature $T_1$ has to be sufficiently high so as to retard such deactivation and permit the continuous alkylation of aromatics at a conversion of at least 98, and preferably greater than 99, percent for rather long periods of time. Stated differently, for continuous operation over substantial periods of time with conversions in excess of 98 percent, and preferably in excess of 99 percent, a concentration of aromatic byproducts in the alkylation feedstock of more than 2 and up to about 10 weight percent necessitates a higher operating temperature than would suffice if such aromatic byproducts were absent. This is an experimentally demonstrable and demonstrated fact which is beyond question. A consequence of the higher alkylation operating temperatures necessitated by the presence of aromatic byproducts in the alkylation feedstock is a decreased linearity of the resulting monoalkyl aromatics, especially the monoalkylbenzenes. A more direct consequence of the presence of aromatic byproducts in the alkylation feedstock is a decreased selectivity (vide supra), which means decreased utilization of the valuable linear monoolefins in high-valued products.

It is highly desirable that sufficient aromatic byproducts having between 7 and about 20 carbons be removed from the alkylation feedstock so as to enable an alkylation operating temperature at least 5° less than that needed in the absence of aromatic byproduct removal, and it is more desirable that the aromatic byproduct concentration in the alkylation feedstock be reduced so as to permit a reduction of alkylation operating temperature of at least 10° C. The concentration of aromatic byproducts which needs to be removed in order to effect such a reduction in alkylation operating temperature depends somewhat on the nature of the aromatic byproducts, for the different aromatic byproducts may be deleterious to differing extents. For example, polynuclear hydrocarbons and their alkylated counterparts may be expected to be more effective in blocking the strong acid sites of solid alkylation catalysts than are, for example, alkylated benzenes of the same carbon number. Consequently, alkylation feedstocks containing aromatic byproducts which are largely polynuclear hydrocarbons may need a larger fraction of such aromatic byproducts removed than is the case when the aromatic byproducts are largely alkylated benzenes. However, we have found that reducing the aromatic byproduct concentration in the alkylation feedstock to less than 2 weight percent provides a noticeable prolongation of catalyst lifetime, reducing the aromatic byproduct concentration to no more than 1 weight percent effects a substantial increase in catalyst life, and decreasing the aromatic byproducts to 0.5 weight percent or less leads to a dramatic increase in catalyst life. It also should be clear that the aromatic byproducts removed have the same carbon number range as the paraffins used for dehydrogenation, since the aromatic byproducts arise from aromatization of the paraffins.

From a commercial aspect it is necessary that a solid alkylation catalyst effect greater than 99% conversion of olefins at a benzene to olefin molar ratio between 5 and 30 for at least 16 hours at a steady space velocity and pressure whose exact values are not important in the context of my invention. The foregoing criteria can be used as a benchmark to evaluate the improvement arising from removal of aromatic byproducts from the alkylation feedstock, especially as to the decrease in temperature made possible without decreasing the catalyst activity.

The foregoing description has been largely specific to solid alkylation catalysts and may not pertain in its entirety to HF as an alkylation catalyst. However, we may expect aromatics byproducts removal to benefit HF-based alkylation processes as well. The aromatic byproducts, especially in the C10–C14 range, are alkylated by linear olefins more efficiently when using HF as the catalyst than when using a solid alkylation catalyst. Consequently, reduction of the aromatic byproducts can be expected to improve alkylation selectivity in an HF-based process to perhaps an even greater extent than is found in a solid catalyst-based process. The aromatic byproducts also are soluble in the HF slipstream used for HF regeneration. Consequently, their reduction can be expected to increase HF stability and to simplify HF regeneration.

The mode and mechanism of reducing the aromatic byproducts concentration in the alkylation feedstock is a matter of choice. For example, one may use solid adsorption processes where the aromatic byproducts are more strongly adsorbed on solid adsorbents than are the other components in the alkylation feedstock. It also may be possible to remove the offending aromatic byproducts using liquid/liquid extraction. It needs to be emphasized again that the particular means of reducing the aromatic byproducts concentration in the alkylation feedstock is secondary to the reduction itself. Our invention focuses on the significant benefits conferred upon a process for alkylating aromatics with linear olefins present in an alkylation feedstock arising from the dehydrogenation of normal paraffins where the alkylation feedstock has an unusually low concentration of aromatic byproducts. Even though the means of obtaining such low concentrations may have independent significance, nonetheless they are here incidental to our invention.

Just as there may be many methods for removing the offending aromatic byproducts, so may there be many designs incorporating these methods in an overall dehydrogenation-alkylation process. For example, aromatic byproducts may be removed from the alkylation feedstock itself. Alternatively, aromatic byproducts may be removed from the recycle stream from the alkylation zone. Other designs also are possible which may in fact have great technical, commercial, and patentable significance, nonetheless, they are ancillary to our invention and may be viewed as largely a matter of choice in the context of our invention which deals solely with the need to reduce the concentration of aromatic byproducts in the alkylation feedstock.

The following examples are illustrative of our invention and are only intended to illustrate the invention without limiting it in any way.

EXAMPLES

All pilot plant tests were conducted in a fixed bed reactor containing a solid acid operating at 120° C., a benzene to olefin feed molar ratio of 25, a pressure of 500 psig, and at 2 hr$^{-1}$ LHSV. The fresh (untreated) feed was obtained from a commercial alkylation unit using HF as the acid catalyst. The composition given in Table 1 is typical of HF alkylation feedstocks for LAB processes with continuous alkylation and paraffin recycle to the dehydrogenation unit. Olefin conversion was monitored by gas chromatographic analysis of the product. The n-paraffins were used as an internal standard for calculating conversion at each carbon number.

TABLE 1

| Commercial Alkylation Feedstock Composition | |
|---|---|
| Linear paraffins and olefins | wt. % |
| C-10 | 13.7 |
| C-10= | 1.7 |
| C-11 | 26.1 |
| C-11= | 3.5 |
| C-12 | 22.2 |
| C-12= | 3.3 |
| C-13 | 14.9 |
| C-13= | 2.8 |
| C-14 | 5.1 |
| C-14= | 0.1 |
| Aromatics | 5.2 |
| Others | 1.4 |

Effect of Aromatics Removal: Adsorption

Alkylation feedstock 2 was prepared by passing the commercial feed continuously over a fixed sorptive bed of 13X molecular sieves at 130° C. and 450 psig to maintain liquid phase. The liquid hourly space velocity was about 2.7 hr$^{-1}$. This was continued until significant aromatics were observed in the product effluent by gas chromatography. Regeneration of the 13X sieves was accomplished by benzene flush at the same conditions. This process was repeated until sufficient feed was available for testing. Treating feed in this manner reduced aromatics from 5.2 to 2.1 weight percent of the paraffin/olefin blend.

Feedstock 3 was prepared by adding the 13X sieve directly into a vessel containing Feed 1. A 50% excess of sieves was used based on the capacity of the sieves determined experimentally. The contents were then stirred at room temperature and atmospheric pressure for about 10 minutes. The liquid and solid was separated by filtration and the liquid product was found to have 0.3 weight percent aromatics content.

Feedstock 4 was prepared by blending appropriate amounts of Feedstock 1 and Feedstock 3 to obtain 1.0 weight percent aromatics content. Analysis also shows no difference in olefin content between these 4 feedstocks.

Table 2 shows the results of pilot plant tests of these 4 feedstocks where the catalyst was a fluorided amorphous silica-alumina. However, the choice of catalyst is not important in demonstrating the effect of aromatics removal. Catalyst life, as defined by hours at 100% olefin conversion using a benzene to olefin feed molar ratio of 25 at a pressure of 250 psig and a LHSV of 2 hr$^{-1}$, increases from 16 hours (1), to 32 (2), to 46 (4), to 100 (3) hours with decreasing amounts of aromatics. Additionally, removing aromatics leads to increased selectivity to monoalkylbenzene from 87.8 to 93.5 weight percent. This increase is realized because benzene is alkylated to the desired product instead of the olefins alkylating the aromatic impurities yielding an undesirable material. The table shows no significant change in linearity at 120° C. (about 94%) as a consequence of aromatics removal. However, using feedstock 3 (0.3% aromatic byproducts) at the same conditions of benzene-to-olefin ratio, pressure and LHSV, a conversion of 100% was maintained for 16 hours at 100° C.-a decrease in operating temperature of 20° C.!-with a linearity of 95.3%. Thus, decreasing the aromatics in the alkylation feedstock permitted operation with an acceptable lifetime at 100° C., leading to an increased linearity of almost 2%.

TABLE 2
Effect of Aromatics Removal

| Feedstock No. | Wt. % Aromatics in Feedstock | % Aromatics Removal | Hours at 100% Conversion | % Linearity | Wt. % Monoalkylate Selectivity |
|---|---|---|---|---|---|
| 1$^b$ | 5.2 | 0 | 16 | 93.9 | 87.8 |
| 2 | 2.1 | 59.6 | 32 | 94.4 | 90.2 |
| 4 | 1.0 | 80.8 | 46 | 94.2 | 92.2 |
| 3 | 0.3 | 94.2 | 100 | 94.0 | 93.5 |
| 3 | 0.3 (100° C.)$^c$ | 94.2 | 16 | 95.3 | 93.4 |

$^a$Reaction conditions: 120° C., 500 psig, LHSV of 2 hr$^{-1}$, and benzene:olefin molar ratio of 25.
$^b$Untreated feedstock.
$^c$Reaction temperature: 100° C.

The above results show that aromatics removal can be used two ways. The catalyst life can be extended at a particular operating temperature with a substantial increase in monoalkylate selectivity, Secondly, operation at lower temperatures is possible to increase product linearity,

Aromatics Removal: Liquid-Liquid Extraction

Two experiments were conducted to remove aromatics from feed to solid bed alkylation unit. Sulfonlane and ethylenediamine were evaluated as solvents to extract the aromatics. Experiments were conducted at room temperature and atmospheric pressure. One volume of alkylation feedstock was extracted with 1 volume of solvent, and after mixing and phase separation a sample of the feedstock was analyzed for aromatics. The remaining material was extracted a second time with fresh solvent. The separation and analysis was repeated. Results are listed below.

| | % AROMATICS | |
|---|---|---|
| | Sulfolane | Ethylenediamine |
| Untreated Pacolate | 4.9 | 4.9 |
| After 1 Extraction | 3.7 | 4.0 |
| After 2 Extractions | 2.7 | 3.3 |

Both solvents showed some capability of removing aromatics from the feedstock. There was no evidence (GC) that any olefin was lost in either solvent. Improved catalyst performance similar to the results in the above example can be expected.

Aromatics Removal: HF Alkylation

Aromatics removal would improve performance of an existing HF unit in at least 2 ways. First, no olefin would be used to alkylate these aromatics; therefore, selectivity to monoalkylate may increase from about 96 to about 98%. Secondly, since less byproduct is formed the HF regeneration section will run less frequently, thereby lowering utility costs for operation. A third possible advantage would be improved stability of the dehydrogenation catalyst due to the removal of aromatics in the recycle stream.

What is claimed is:

1. A process of increasing the linearity of monoalkylbenzenes formed in the continuous alkylation of benzene by the linear monoolefins contained in an alkylation feedstock arising from the dehydrogenation of linear paraffins having from 6 to 20 carbon atoms and consisting essentially of unreacted linear paraffins, linear olefins, and more than about 2 weight percent of aromatic compounds formed in said dehydrogenation having from about 7 up through about 20 carbon atoms, said alkylation performed in the presence of an alkylation catalyst at a benzene to olefin molar ratio R, a liquid hourly space velocity L, a pressure P, and at a temperature $T_1$, where said alkylation catalyst effects more than 99% conversion of olefins for a time $t_1$ which is at least 16 hours, said process comprising decreasing the concentration of the aromatic compounds in the alkylation feedstock to less than about 2 weight percent to afford a reduced aromatics alkylation feedstock, and subsequently performing said alkylation with the reduced aromatics alkylation feedstock under the same R, L, and P values but at a temperature $T_2$ at least 5° C. lower than $T_1$, and where said alkylation catalyst effects more than 99% conversion of olefins for a time $t_2$ which is at least as great as $t_1$.

2. The process of claim 1 where the concentration of aromatic compounds in the reduced aromatics alkylation feedstock is less than about 1 weight percent.

3. The process of claim 1 where the concentration of aromatic byproducts in the reduced aromatics alkylation feedstock is less than about 0.5 weight percent.

4. The process of claim 1 where the alkylation feedstock arises from the dehydrogenation of at least one linear paraffin having from 8 up to 16 carbon atoms.

5. The process of claim 1 where the alkylation feedstock arises from the dehydrogenation of linear paraffins having from 8 to 16 carbon atoms.

6. The process of claim 1 where the alkylation feedstock arises from the dehydrogenation of linear paraffins having from 10 to 14 carbon atoms.

7. The process of claim 1 where the alkylation catalyst is a solid alkylation catalyst.

8. The process of claim 1 where the alkylation catalyst is HF.

9. The process of claim 1 where the alkylation feedstock arises from the dehydrogenation of normal paraffins having from 10 to 14 carbon atoms, the concentration of aromatic compounds having from 7 up to about 20 carbon atoms in the reduced aromatics alkylation feedstock is less than 2 weight percent, and $T_2$ is at least 10° C. lower than T.

10. In the process of preparing linear monoalkylbenzenes by the continuous alkylation of benzene with the linear monoolefins contained in a first alkylation feedstock, said first alkylation feedstock arising from the dehydrogenation of linear paraffins having from 6 to 20 carbon atoms and consisting essentially of unreacted linear paraffins, olefins and at least two weight percent aromatic compounds formed in said dehydrogenation having from about 7 up through about 20 carbon atoms, where said alkylation is performed in the presence of an alkylation catalyst at a temperature $T_1$, the improvement comprising decreasing the concentration of the aromatic compounds in the first alkylation feedstock to produce a second alkylation feedstock containing less than 2 weight percent of aromatic compounds, and reacting the second alkylation feedstock with benzene at a temperature $T_2$ which is at least 5° C. lower than the temperature $T_1$ to afford monoalkylbenzenes of higher linearity.

11. The process of claim 10 where the concentration of aromatic compounds in the second alkylation feedstock is less than about 1 weight percent.

12. The process of claim 10 where the concentration of aromatic byproducts in the second alkylation feedstock is less than about 0.5 weight percent.

13. The process of claim 10 where the first alkylation feedstock arises from the dehydrogenation of at least one linear paraffin having from 8 up to 16 carbon atoms.

14. The process of claim 10 where the first alkylation feedstock arises from the dehydrogenation of linear paraffins having from 8 to 16 carbon atoms.

15. The process of claim 10 where the first alkylation feedstock arises from the dehydrogenation of linear paraffins having from 10 to 14 carbon atoms.

16. The process of claim 10 where the alkylation catalyst is a solid alkylation catalyst.

17. The process of claim 10 where the alkylation catalyst is HF.

18. The process of claim 10 where the first alkylation feedstock arises from the dehydrogenation of normal paraffins having from 10 to 14 carbon atoms, the concentration of aromatic compounds having from 7 up to about 20 carbon atoms in the second alkylation feedstock is less than 2 weight percent, and $T_2$ is at least 10° C. lower than T.

* * * * *